(12) United States Patent
Gefen et al.

(10) Patent No.: US 8,702,620 B2
(45) Date of Patent: Apr. 22, 2014

(54) REMOTE PRESSURE SENSING SYSTEM AND METHOD THEREOF

(75) Inventors: Ra'anan Gefen, Reut (IL); Tal Sheps, Givat Shmuel (IL); Reuven Eshel, Haifa (IL); Ran Mendelewicz, Herzliya (IL); Noam Kinrot, Nesher (IL)

(73) Assignee: G.I. View Ltd., Ramat Gan (IL)

( * ) Notice: Subject to any disclaimer, the term of this patent is extended or adjusted under 35 U.S.C. 154(b) by 71 days.

(21) Appl. No.: 13/126,829

(22) PCT Filed: Nov. 3, 2009

(86) PCT No.: PCT/IL2009/001027
§ 371 (c)(1),
(2), (4) Date: Aug. 23, 2011

(87) PCT Pub. No.: WO2010/061379
PCT Pub. Date: Jun. 3, 2010

(65) Prior Publication Data
US 2011/0295146 A1     Dec. 1, 2011

(51) Int. Cl.
| A61M 31/00 | (2006.01) |
| A61B 5/00 | (2006.01) |
| A61N 1/30 | (2006.01) |
| A61M 1/00 | (2006.01) |
| A61B 18/18 | (2006.01) |

(52) U.S. Cl.
USPC ........... 600/560; 600/481; 600/485; 600/488; 600/561; 604/21; 604/27; 606/21

(58) Field of Classification Search
USPC ......... 600/560, 561, 481, 485, 488, 587, 593; 606/21; 604/21, 27
See application file for complete search history.

(56) References Cited

U.S. PATENT DOCUMENTS

| 3,895,637 A | 7/1975 | Choy |
| 3,924,625 A | 12/1975 | Peterson |

(Continued)

FOREIGN PATENT DOCUMENTS

| DE | 3630660 A1 | 3/1988 |
| EP | 0242428 | 10/1987 |

(Continued)

OTHER PUBLICATIONS

U.S. Appl. No. 60/490,038, filed Jul. 24, 2003, James, Benjamin B.

(Continued)

*Primary Examiner* — Rene Towa
*Assistant Examiner* — May Abouelela
(74) *Attorney, Agent, or Firm* — Frommer Lawrence & Haug LLP; William S. Frommer

(57) ABSTRACT

The present invention relates to a monitoring system and method for use with a body of a subject. The system comprises a medical device, having a portion thereof configured to be placed inside the subject's body, said portion of the medical device being configured to be propelled by fluid pressure through a body lumen; at least two pressure sensors accommodated remotely from the subject's body at two different spaced-apart positions outside the subject's body and configured and operable to detect pressure at the two spaced-apart remote positions; said at least two pressure sensors being in fluid communication with at least one site inside the subject's body, a relation between the pressure at said at least one site and the pressures at said two spaced-apart remote positions being thereby indicative of the fluid pressure at said at least one site.

15 Claims, 9 Drawing Sheets

(56) References Cited

U.S. PATENT DOCUMENTS

| | | | |
|---|---|---|---|
| 4,040,413 A | 8/1977 | Ohshiro | |
| 4,066,070 A | 1/1978 | Utsugi | |
| 4,077,610 A | 3/1978 | Masuda | |
| 4,148,307 A | 4/1979 | Utsugi | |
| 4,176,662 A | 12/1979 | Frazer | |
| 4,207,872 A | 6/1980 | Meiri et al. | |
| 4,224,929 A | 9/1980 | Furihata | |
| 4,278,077 A | 7/1981 | Mizumoto | |
| 4,306,446 A | 12/1981 | Fukuda | |
| 4,327,722 A | 5/1982 | Groshong et al. | |
| 4,403,985 A | 9/1983 | Boretos | |
| 4,502,490 A * | 3/1985 | Evans et al. | 600/593 |
| 4,530,698 A | 7/1985 | Goldstein et al. | |
| 4,561,427 A | 12/1985 | Takada | |
| 4,566,763 A | 1/1986 | Greguss | |
| 4,596,381 A | 6/1986 | Hamrick | |
| 4,690,131 A | 9/1987 | Lyddy, Jr. et al. | |
| 4,737,142 A | 4/1988 | Heckele | |
| 4,838,859 A | 6/1989 | Strassmann | |
| 4,971,034 A * | 11/1990 | Doi et al. | 600/104 |
| 4,976,524 A | 12/1990 | Chiba | |
| 4,995,396 A | 2/1991 | Inaba et al. | |
| 5,246,419 A * | 9/1993 | Absten | 604/26 |
| 5,247,938 A * | 9/1993 | Silverstein et al. | 600/459 |
| 5,259,364 A | 11/1993 | Bob et al. | |
| 5,337,732 A * | 8/1994 | Grundfest et al. | 600/116 |
| 5,353,807 A | 10/1994 | DeMarco | |
| 5,360,396 A * | 11/1994 | Chan | 604/26 |
| 5,364,353 A | 11/1994 | Corfitsen et al. | |
| 5,395,332 A | 3/1995 | Ressemann et al. | |
| 5,398,670 A | 3/1995 | Ortiz et al. | |
| 5,471,988 A | 12/1995 | Fujio et al. | |
| 5,473,474 A | 12/1995 | Powell | |
| 5,476,505 A | 12/1995 | Limon | |
| 5,509,371 A | 4/1996 | Phillips | |
| 5,571,114 A | 11/1996 | Devanaboyina | |
| 5,575,754 A | 11/1996 | Konomura | |
| 5,586,968 A | 12/1996 | Grundl et al. | |
| 5,586,973 A | 12/1996 | Lemaire et al. | |
| 5,604,531 A | 2/1997 | Iddan et al. | |
| 5,660,198 A * | 8/1997 | McClaran | 137/12 |
| 5,662,587 A | 9/1997 | Grundfest et al. | |
| 5,728,068 A | 3/1998 | Leone et al. | |
| 5,740,808 A * | 4/1998 | Panescu et al. | 600/424 |
| 5,863,284 A | 1/1999 | Klein | |
| 5,879,325 A | 3/1999 | Lindstrom et al. | |
| 5,906,357 A | 5/1999 | Munson, Sr. | |
| 5,906,591 A | 5/1999 | Dario et al. | |
| 5,910,105 A | 6/1999 | Swain et al. | |
| 5,941,815 A | 8/1999 | Chang | |
| 5,984,860 A | 11/1999 | Shan | |
| 6,028,719 A | 2/2000 | Beckstead et al. | |
| 6,071,234 A | 6/2000 | Takada | |
| 6,130,783 A | 10/2000 | Yagi et al. | |
| 6,157,018 A | 12/2000 | Ishiguro et al. | |
| 6,162,182 A * | 12/2000 | Cole | 600/486 |
| 6,171,252 B1 * | 1/2001 | Roberts | 600/485 |
| 6,261,227 B1 * | 7/2001 | Takahashi et al. | 600/158 |
| 6,277,065 B1 | 8/2001 | Donofrio | |
| 6,296,608 B1 | 10/2001 | Daniels et al. | |
| 6,299,592 B1 * | 10/2001 | Zander | 604/26 |
| 6,315,713 B1 | 11/2001 | Takada | |
| 6,322,514 B1 * | 11/2001 | Holte | 600/481 |
| 6,332,865 B1 | 12/2001 | Borody et al. | |
| 6,333,826 B1 | 12/2001 | Charles | |
| 6,341,044 B1 | 1/2002 | Driscoll, Jr. et al. | |
| 6,356,296 B1 | 3/2002 | Driscoll, Jr. et al. | |
| 6,373,642 B1 | 4/2002 | Wallerstein et al. | |
| 6,388,820 B1 | 5/2002 | Wallerstein et al. | |
| 6,402,688 B1 * | 6/2002 | Takami et al. | 600/158 |
| 6,402,714 B1 * | 6/2002 | Kraft-Kivikoski | 604/23 |
| 6,422,989 B1 | 7/2002 | Hektner | |
| 6,424,377 B1 | 7/2002 | Driscoll, Jr. et al. | |
| 6,439,032 B1 | 8/2002 | Lehmann | |
| 6,449,103 B1 | 9/2002 | Charles | |
| 6,459,451 B2 | 10/2002 | Driscoll, Jr. et al. | |
| 6,471,656 B1 * | 10/2002 | Shalman et al. | 600/486 |
| 6,485,409 B1 | 11/2002 | Voloshin et al. | |
| 6,493,032 B1 | 12/2002 | Wallerstein et al. | |
| 6,503,192 B1 | 1/2003 | Ouchi | |
| 6,517,477 B1 | 2/2003 | Wendlandt | |
| 6,527,705 B1 | 3/2003 | Ouchi | |
| 6,537,206 B2 | 3/2003 | Takada | |
| 6,544,216 B1 | 4/2003 | Sammler et al. | |
| 6,587,724 B2 | 7/2003 | Mann | |
| 6,597,520 B2 | 7/2003 | Wallerstein et al. | |
| 6,599,237 B1 | 7/2003 | Singh | |
| 6,609,032 B1 | 8/2003 | Woods et al. | |
| 6,611,282 B1 | 8/2003 | Trubko et al. | |
| 6,632,227 B2 | 10/2003 | Adams | |
| 6,645,197 B2 * | 11/2003 | Garrison et al. | 606/1 |
| 6,646,818 B2 | 11/2003 | Doi | |
| 6,648,814 B2 | 11/2003 | Kim et al. | |
| 6,682,479 B1 * | 1/2004 | Takahashi et al. | 600/159 |
| 6,695,771 B2 | 2/2004 | Takada | |
| 6,702,734 B2 | 3/2004 | Kim et al. | |
| 6,702,735 B2 | 3/2004 | Kelly | |
| 6,704,148 B2 | 3/2004 | Kumata | |
| 6,709,388 B1 | 3/2004 | Mosse et al. | |
| 6,743,208 B1 | 6/2004 | Coyle | |
| 6,764,441 B2 | 7/2004 | Chiel et al. | |
| 6,786,864 B2 | 9/2004 | Matsuura et al. | |
| 6,800,056 B2 | 10/2004 | Tartaglia et al. | |
| 6,814,728 B2 | 11/2004 | Ouchi | |
| 6,824,510 B2 | 11/2004 | Kim et al. | |
| 6,827,718 B2 | 12/2004 | Hutchins et al. | |
| 6,837,846 B2 | 1/2005 | Jaffe et al. | |
| 6,866,626 B2 | 3/2005 | Long et al. | |
| 6,869,393 B2 | 3/2005 | Butler | |
| 6,872,183 B2 * | 3/2005 | Sampson et al. | 600/561 |
| 6,911,005 B2 | 6/2005 | Ouchi et al. | |
| 6,932,323 B2 | 8/2005 | James | |
| 6,974,441 B2 | 12/2005 | Ravo | |
| 7,056,283 B2 | 6/2006 | Baror et al. | |
| 7,063,670 B2 * | 6/2006 | Sampson et al. | 600/560 |
| 7,156,840 B2 * | 1/2007 | Lentz et al. | 606/21 |
| 7,204,798 B2 * | 4/2007 | Zdeblick et al. | 600/17 |
| 7,422,587 B2 * | 9/2008 | Bek et al. | 606/41 |
| 7,427,265 B1 * | 9/2008 | Keilman et al. | 600/300 |
| 7,481,774 B2 * | 1/2009 | Brockway et al. | 600/561 |
| 7,527,622 B2 * | 5/2009 | Lane et al. | 606/21 |
| 7,635,345 B2 * | 12/2009 | Gross et al. | 604/99.01 |
| 7,666,220 B2 * | 2/2010 | Evans et al. | 623/1.25 |
| 7,695,428 B2 * | 4/2010 | Machida | 600/114 |
| 7,722,559 B2 * | 5/2010 | Uesugi et al. | 604/26 |
| 7,727,228 B2 * | 6/2010 | Abboud et al. | 606/21 |
| 7,833,176 B2 * | 11/2010 | Gross et al. | 600/585 |
| 7,905,879 B2 * | 3/2011 | Abboud et al. | 606/22 |
| 7,947,013 B2 * | 5/2011 | Cabiri et al. | 604/99.01 |
| 8,491,636 B2 * | 7/2013 | Abboud et al. | 606/251 |
| 8,545,491 B2 * | 10/2013 | Abboud et al. | 606/22 |
| 2001/0041874 A1 | 11/2001 | Reydel | |
| 2002/0012059 A1 | 1/2002 | Wallerstein et al. | |
| 2002/0065472 A1 * | 5/2002 | Brockway et al. | 600/486 |
| 2002/0072651 A1 | 6/2002 | Vilos | |
| 2002/0077759 A1 * | 6/2002 | Cohen et al. | 702/50 |
| 2002/0107478 A1 * | 8/2002 | Wendlandt | 604/95.01 |
| 2002/0109772 A1 | 8/2002 | Kuriyama et al. | |
| 2002/0109773 A1 | 8/2002 | Kuriyama et al. | |
| 2003/0000526 A1 | 1/2003 | Gobel | |
| 2003/0074015 A1 | 4/2003 | Nakao | |
| 2003/0083547 A1 * | 5/2003 | Hamilton et al. | 600/116 |
| 2003/0100845 A1 * | 5/2003 | Eide | 600/561 |
| 2003/0105386 A1 | 6/2003 | Voloshin et al. | |
| 2003/0153866 A1 | 8/2003 | Long et al. | |
| 2003/0167031 A1 * | 9/2003 | Odland | 604/8 |
| 2003/0168068 A1 | 9/2003 | Poole et al. | |
| 2003/0181788 A1 | 9/2003 | Yokoi et al. | |
| 2003/0191369 A1 | 10/2003 | Arai et al. | |
| 2003/0208219 A1 | 11/2003 | Aznoian et al. | |
| 2003/0225433 A1 | 12/2003 | Nakao | |
| 2004/0004836 A1 | 1/2004 | Dubuc | |
| 2004/0111010 A1 | 6/2004 | Nishiie | |
| 2004/0111019 A1 | 6/2004 | Long | |

(56) References Cited

U.S. PATENT DOCUMENTS

| | | | |
|---|---|---|---|
| 2004/0111020 A1* | 6/2004 | Long | 600/407 |
| 2004/0138586 A1* | 7/2004 | Ganz et al. | 600/560 |
| 2004/0143161 A1 | 7/2004 | Baror et al. | |
| 2004/0171942 A1* | 9/2004 | Ackerman et al. | 600/486 |
| 2004/0199087 A1 | 10/2004 | Swain et al. | |
| 2004/0199088 A1 | 10/2004 | Bakos et al. | |
| 2004/0199196 A1 | 10/2004 | Ravo | |
| 2004/0204702 A1 | 10/2004 | Ziegler et al. | |
| 2004/0249247 A1 | 12/2004 | Iddan | |
| 2004/0260150 A1* | 12/2004 | Bernstein | 600/139 |
| 2005/0038317 A1 | 2/2005 | Ratnakar | |
| 2005/0038319 A1 | 2/2005 | Goldwasser et al. | |
| 2005/0065450 A1* | 3/2005 | Stuebe et al. | 600/547 |
| 2005/0085841 A1 | 4/2005 | Eversull et al. | |
| 2005/0095200 A1 | 5/2005 | Schwarzberg | |
| 2005/0107664 A1 | 5/2005 | Kalloo et al. | |
| 2005/0154355 A1* | 7/2005 | Gross et al. | 604/232 |
| 2005/0165272 A1 | 7/2005 | Okada et al. | |
| 2005/0187546 A1* | 8/2005 | Bek et al. | 606/41 |
| 2005/0215989 A1* | 9/2005 | Abboud et al. | 606/21 |
| 2005/0222535 A1* | 10/2005 | Uesugi et al. | 604/26 |
| 2006/0030843 A1* | 2/2006 | Lane et al. | 606/21 |
| 2006/0100495 A1* | 5/2006 | Santoianni et al. | 600/374 |
| 2006/0111611 A1 | 5/2006 | Eizenfeld et al. | |
| 2006/0164733 A1 | 7/2006 | Gal et al. | |
| 2006/0238879 A1* | 10/2006 | Togino | 359/637 |
| 2006/0287577 A1* | 12/2006 | Wendlandt | 600/146 |
| 2007/0032783 A1* | 2/2007 | Abboud et al. | 606/21 |
| 2007/0255162 A1* | 11/2007 | Abboud et al. | 600/547 |
| 2007/0255165 A1* | 11/2007 | Uesugi et al. | 600/560 |
| 2008/0114345 A1* | 5/2008 | Arless et al. | 606/20 |
| 2008/0200829 A1* | 8/2008 | Abboud et al. | 600/547 |
| 2008/0215043 A1* | 9/2008 | Abboud et al. | 606/21 |
| 2009/0030288 A1* | 1/2009 | Abboud et al. | 600/300 |
| 2009/0088735 A1* | 4/2009 | Abboud et al. | 606/22 |
| 2009/0118722 A1* | 5/2009 | Ebbers et al. | 606/21 |
| 2009/0182318 A1* | 7/2009 | Abboud et al. | 606/21 |
| 2009/0203995 A1* | 8/2009 | Matonick | 600/435 |
| 2009/0287201 A1* | 11/2009 | Lalonde et al. | 606/21 |
| 2010/0114269 A1* | 5/2010 | Wittenberger et al. | 607/105 |
| 2011/0077550 A1* | 3/2011 | Bek et al. | 600/561 |

FOREIGN PATENT DOCUMENTS

| | | |
|---|---|---|
| EP | 0267446 | 10/1987 |
| EP | 0659387 | 12/1994 |
| EP | 1586275 | 4/2005 |
| FR | 1465723 A | 3/1967 |
| JP | 03-009726 | 1/1991 |
| JP | 03-295657 | 12/1991 |
| JP | 5-43114 | 6/1993 |
| JP | 06-173878 | 6/1994 |
| JP | 7313443 | 12/1995 |
| JP | 10216076 | 8/1998 |
| JP | 10309259 | 11/1998 |
| JP | 2002031766 | 1/2002 |
| JP | 2002-148246 | 5/2002 |
| JP | 2006026344 | 2/2006 |
| JP | 2008-531096 | 8/2008 |
| WO | WO9940957 | 8/1999 |
| WO | WO0168540 A2 | 9/2001 |
| WO | WO02059676 A1 | 8/2002 |
| WO | WO02068035 A1 | 9/2002 |
| WO | WO02075348 A2 | 9/2002 |
| WO | WO03026272 A2 | 3/2003 |
| WO | WO03045487 A2 | 6/2003 |
| WO | WO03046830 A2 | 6/2003 |
| WO | WO03053225 A1 | 7/2003 |
| WO | WO2004008185 A2 | 1/2004 |
| WO | WO2004010858 A2 | 2/2004 |
| WO | WO2004016299 A2 | 2/2004 |
| WO | WO2004028354 A1 | 4/2004 |
| WO | WO2004049905 A2 | 6/2004 |
| WO | WO2004069057 A2 | 8/2004 |
| WO | WO 2005/065044 | 7/2005 |
| WO | WO2006025045 A1 | 3/2006 |
| WO | WO 2006089811 | 8/2006 |
| WO | WO 2006/130422 | 12/2006 |

OTHER PUBLICATIONS

Japanese Office Action dated Nov. 19, 20133.

* cited by examiner

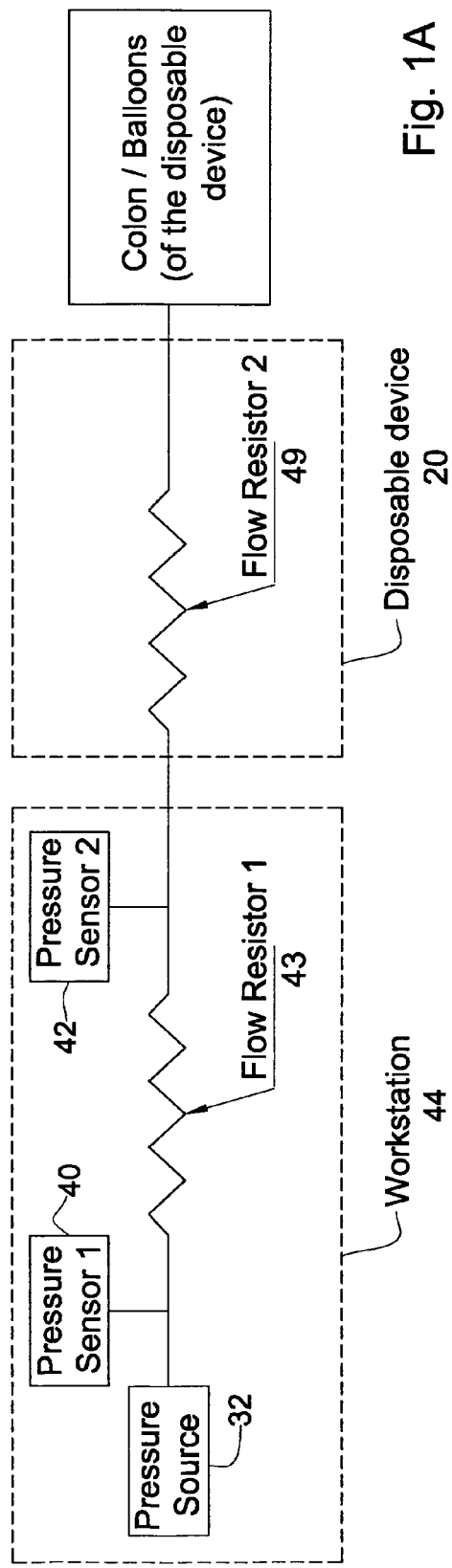
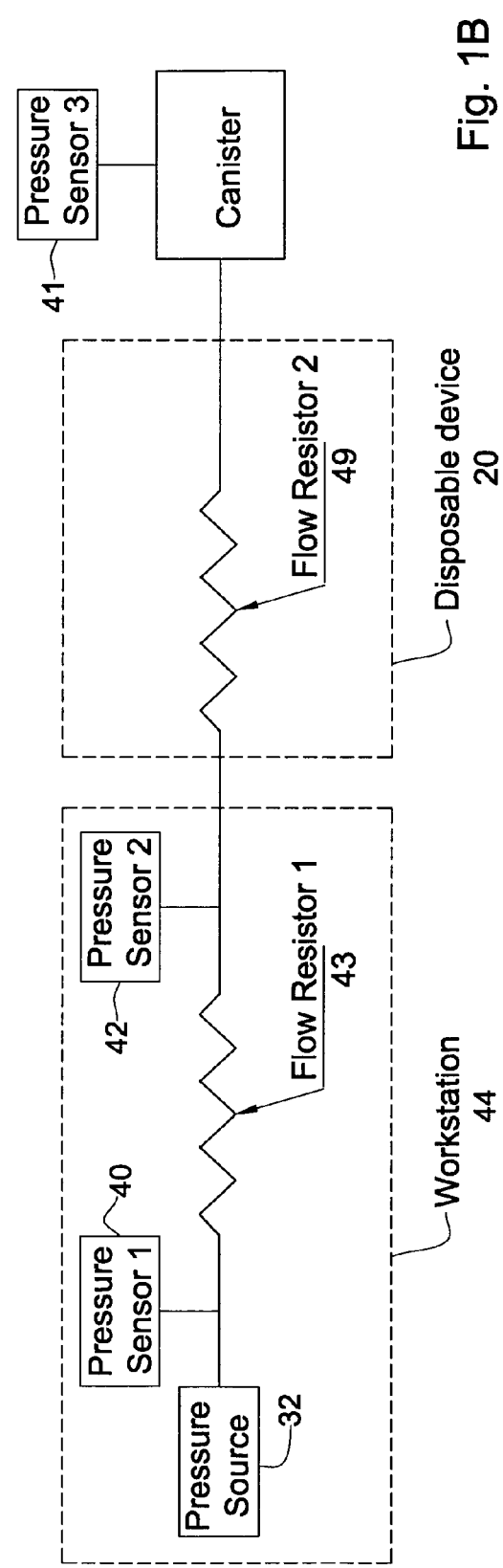

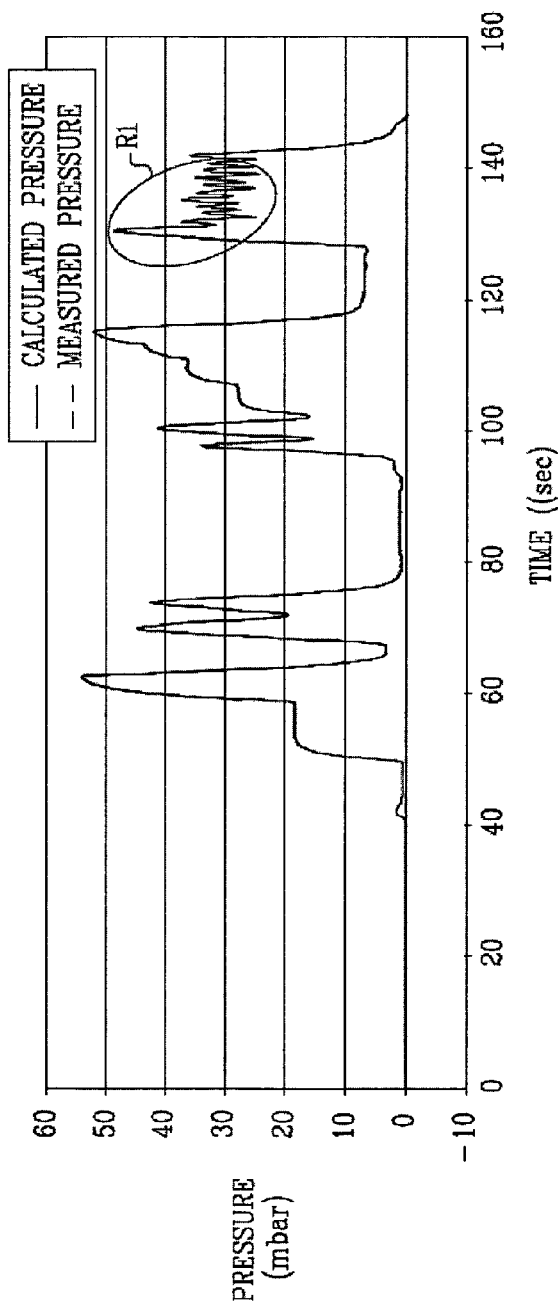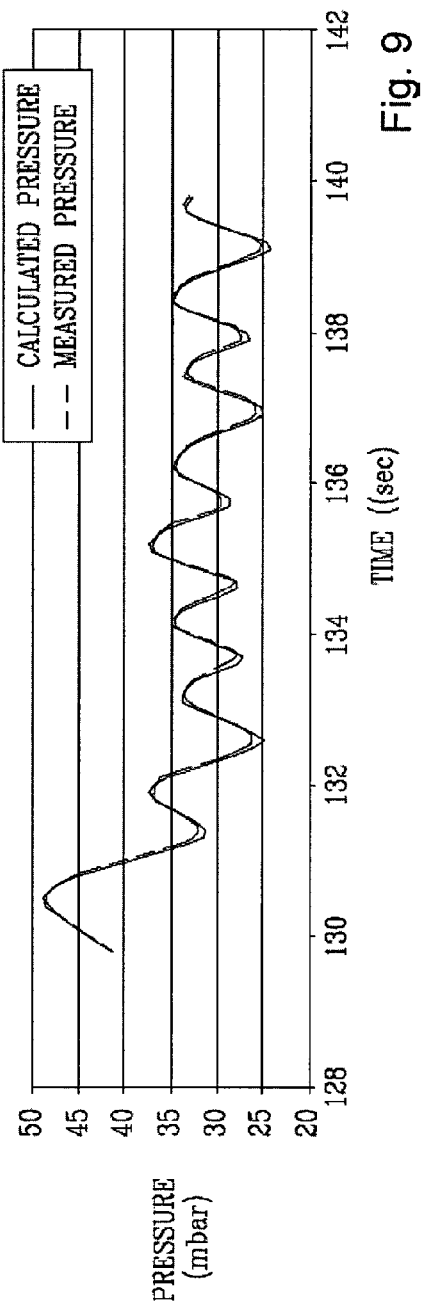
Fig. 8
Fig. 9

REMOTE PRESSURE SENSING SYSTEM AND METHOD THEREOF

FIELD OF THE INVENTION

The present invention generally relates to medical system. Specifically, the present invention relates to a remote sensing pressure of medical system.

BACKGROUND OF THE INVENTION

There are many examples of medical devices having distal portions for inserting into subjects' bodies. For example, the distal portion of an endoscope is advanced into a body lumen (such as the gastrointestinal tract) in order to visualize and/or record an image from inside the lumen. A colonoscope is an endoscope, a distal portion of which is inserted into the colon for visualizing and/or recording an image of the colon.

PCT Publication WO 05/065044 to Cabiri et al., describes apparatus for use with a biologically compatible fluid pressure source. The apparatus includes an elongate carrier, adapted to be inserted through a proximal opening of a body lumen, and a piston head coupled to a distal portion of the carrier. The piston head is adapted to form a pressure seal with a wall of the lumen after the carrier has been inserted into the lumen, and to be advanced distally through the body lumen in response to pressure from the fluid pressure source. The apparatus is configured to facilitate distal advancement of the piston head by facilitating passage of fluid out of the lumen from a site within the lumen distal to the piston head. The apparatus additionally includes an optical system, coupled to the carrier in a vicinity of the distal portion, the optical system having distal and proximal ends.

U.S. Pat. No. 4,306,446 to Fukuda describes apparatus for estimating the locality of a leaking spot in a pipeline which conveys a fluid, the apparatus comprising: a pair of detectors located on the pipeline at positions spaced from each other by a certain distance and adapted to detect pressures and pressure gradients at the respective positions; and an operating unit adapted to calculate the locality of a leaking spot on the basis of the pressure gradients and mean pressures as obtained by memory-holding the pressures.

U.S. Pat. No. 5,660,198 to Maclaren, describes a control system for monitoring and regulating fluid pressure at a remote and/or potentially hazardous location along the length of a fluid flow conduit, without requiring a pressure sensor device at the remote site. The control system comprises a controller responsive to fluid pressure and flow rate readings taken at a convenient and/or safe location along the length of the flow conduit, to derive fluid pressure at the remote site. The controller provides a display of the derived pressure and/or operates a control valve at the safe site to regulate the pressure at the remote site.

GENERAL DESCRIPTION

There is a need in the art to provide a monitoring system for use with a body of a subject for controlling operation of a medical device which is propelled by fluid pressure through a body lumen, by monitoring and regulating fluid pressure at a remote location from the body lumen, without requiring a pressure sensor device to be placed within the body lumen.

It should be understood that generally, the distal portion of the medical device of the kind specified being configured to be placed inside the subject's body, has to be highly disinfected or sterile and preferably also disposable. To control the operation of the medical device, the medical device may be coupled to and operated by an external workstation. The workstation typically comprises a control unit, which is typically a general-purpose CPU, and one or more sources of fluid (i.e., liquid or gas) positive and/or negative pressure, as described hereinbelow. When the source(s) of fluid is/are operated, the body lumen and balloon(s) are inflated at predetermined pressures. To accurately control the advancement of the medical device through the body lumen, such as the gastrointestinal (GI) tract, the pressure inside the body lumen and within the one or more balloons propelling the medical device has to be continuously controlled.

Embodiments of the invention are described hereinbelow with reference to the GI tract, but it is understood that these embodiments as well as the inventive concept in general are not limited to use with the GI tract, and may be used for other body lumens as well.

Generally, there are several well-known techniques associated with mathematical equations, determining pressure at a remote site using at least one pressure sensor. Theses techniques use also a flow rate sensor to calculate a system flow coefficient, to thereby enabling meaningful use of the mathematical equations.

The present invention eliminates the requirement of using any flow rate sensor, which, if used, increases the overall error of the monitoring procedure. In addition, once calibrated, there is no need to calculate the system flow coefficient (Cv). According to the teachings of the present invention, the flow is taken into account by a simple polynomial equation considering the resistance of the lines leading to the remote site (piston head or auxiliary balloons). The pressure(s) are measured at a "safe" site, outside the body of the subject (patient) and therefore, the system and the method of the present invention provides a much easier, cost effective and more accurate technique.

There is thus provided, in accordance with an embodiment of the present invention, a monitoring system for use with a body of a subject, the system comprising: a medical device, having a portion thereof configured to be placed inside the subject's body, the portion of the medical device being configured to be propelled by fluid pressure through a body lumen; at least two pressure sensors accommodated remotely from the subject's body at two different spaced-apart positions outside the subject's body and configured and operable to detect pressure at the two spaced-apart remote positions; the at least two pressure sensors being in fluid communication with at least one site inside the subject's body, a relation between the pressure at the at least one site and the pressures at the two spaced-apart remote positions being thereby indicative of the fluid pressure at the at least one site.

In some embodiments, the system comprises a control unit for monitoring and regulating fluid pressure at the at least one site; the control unit being configured and operable to generate an output data indicative of a pressure level at the at least one site, utilizing at least one model defining the relation between the pressure at the at least one site the pressures detected at the two spaced-apart remote positions. The model may utilize a relation between a pressure drop across a resistor defined by a path inside the fluid communication connecting between the at least two pressure sensors.

In some embodiments, the system comprises at least one tubular-like member or conduit connecting between the at least two pressure sensors; the tubular-like member being configured and operable as a flow resistor; the at least two pressure sensors measuring a pressure drop across the resistor. It should be noted that the tubular-like member cross-section does not necessarily have to be circular.

The relation between the pressure at the at least one site and the pressures at the two spaced-apart remote positions may be based on a mathematical function including a polynomial equation taking into account the resistance of the at least one tubular-like member. In an embodiment, the medical device is disposable.

In an embodiment, the medical device is configured as a two-part device, the two parts being attachable to one another, thereby enabling the part of the device containing the portion which is to be placed inside the subject's body, to be disposable.

In an embodiment, the control unit is integrated in an external workstation. The workstation may comprise one or more fluid pressure sources in fluid communication with the portion of the device. The one or more source of fluid pressure source may be configured and operable to inflate the at least one site at predetermined pressures. The medical device includes a guide member at least partially insertable into a body lumen, the guide member including a first passageway connectable to a source of fluid pressure, and at least one inflatable balloon in fluid communication with the guide member. The at least one inflatable balloon is configured and operable to propel the medical device in a distal direction in the body lumen.

The inventors of the present invention have developed a system and method to control the pressure inside the body lumen and within the one or more balloons propelling the medical device outside the body lumen. The pressure within inside the body lumen and within the one or more balloons is evaluated by measuring and processing a pressure gradient on flow resistor being integrated inside the workstation.

In some embodiments of the present invention, the two remote spaced-apart positions are at the proximal and distal ends of a tubular-like member that is disposed within the proximal portion of the device and that acts as a flow resistor.

In some embodiments, the control unit generates, as the output data for the pressure of the distal portion of the device, a value that varies linearly or non-linearly with respect to an arithmetic difference between the pressures detected at the two remote spaced-apart positions. For example, the pressure of the distal portion of the device may be determined by multiplying by a calibration factor the arithmetic difference between the pressures detected at the two remote spaced apart positions, and/or the square of the arithmetic difference.

In some embodiments, the device is placed inside a GI tract lumen of the subject. For example, the device may be a colonoscope.

In an embodiment, the pressure at the distal portion of the device is substantially equal to a pressure of a portion of the subject's body, and the control unit is configured to generate an output data indicative of the pressure of the portion of the subject's body by generating the output data indicative of the pressure at the distal portion of the device.

In an embodiment, the portion of the subject's body includes a colon of the subject, and the control unit is configured to generate an output data indicative of a pressure of the subject's colon by generating the output data indicative of the pressure at the distal portion of the device.

In an embodiment, the system further includes one or more source of fluid pressure in fluid communication with the distal portion of the device, configured to regulate the pressure at the distal portion of the device. In an embodiment, one or more fluid pressure sources are configured to regulate the pressure in the device in response to the output data.

It should be noted that the control unit may use one model when fluid is moving in two different directions between the fluid pressure source and the distal portion of the device and obtain accurate results. However, if needed, in an embodiment, the control unit may be configured to generate the output data utilizing two different models, when fluid is moving in two different directions between the fluid pressure source and the distal portion of the device.

In an embodiment, the control unit is configured to switch between two different models based on two different directions of fluid between the fluid pressure source and the device.

In an embodiment, the device includes a piston head configured to: be inflated so as to form and maintain a pressure seal with a wall of the GI tract lumen, and be advanced distally through the GI tract in response to fluid pressure from the fluid pressure source applied to an external surface of the piston head.

In an embodiment, the at least one site comprises at least one of the followings: at least one inflatable balloon being configured and operable to propel the medical device through the body lumen, a piston head propelling the medical device through the body lumen; a portion of a body lumen.

In an embodiment, the control unit is configured to generate the output data indicative of the pressure at the distal portion of the device, utilizing a model based upon ratio between a resistance of the distal flow path to fluid flow, to a resistance of the tube to fluid flow, when the a distal flow path is defined between a portion of the device extending from the second position to the distal portion of the device.

In an embodiment, the device includes a fluid pressure source, and the distal portion of the device includes a distal end of a passageway, the passageway being configured to convey fluid from the fluid pressure source into a body lumen of the subject.

There is further provided, in accordance with an embodiment of the present invention, a method for use in monitoring operation of a medical device applicable to inside of a body of a subject, the method comprising: providing fluid communication between two different remote spaced-apart positions outside the subject's body and at least one site inside the subject's body; detecting pressure at the two different remote spaced-apart positions; and analyzing the pressure detected at the remote positions, determining a relation between them being indicative of a pressure level at the at least one site, and generating an output data indicative of the pressure level at the at least one site being remote from the at least two positions.

In some embodiments, generating the output data indicative of the pressure level comprises, utilizing at least one model defining the relation between the pressure at the at least one site the pressures detected at the two spaced-apart remote positions. The relation may be based on a mathematical function including a polynomial equation taking into account the resistance of the at least one tubular-like member.

In some embodiments, the method comprises inflating at least one site at predetermined pressures.

In some embodiments, the method comprises identifying whether there is laminar or turbulent fluid flow through the device.

In some embodiments, generating the output data indicative of the pressure level comprises generating a value that varies linearly or non-linearly with respect to an arithmetic difference between the pressures detected at the two remote spaced apart positions.

In some embodiments, the method comprises providing a pressure drop between the two remote positions, for example by providing the pressure drop comprises placing a tubular-like member between the two remote positions.

In some embodiments, generating the output data comprises generating an output data indicative of a pressure of a portion of the subject's body in which the device is disposed. The portion of the subject's body may include a colon of the subject.

In some embodiments, the method comprises regulating the pressure within the device for example by regulating the pressure in response to the output data.

In some embodiments, generating the output data comprises utilizing two different models relating the pressure within the device to respective relations of the pressures detected at the two remote positions, when fluid is moving in respective two different directions between a fluid pressure source and the device.

In some embodiments, generating the output data comprises determining a direction of fluid flow, and changing the model that is utilized to generate the output data accordingly.

In some embodiments, generating the output data indicative of the pressure within the device comprises generating a value that varies with respect to a square of the arithmetic difference between the pressures detected at the two remote positions.

In some embodiments, placing the device inside the subject's body comprises placing a distal portion of the device inside a gastrointestinal (GI) tract lumen of the subject.

In some embodiments, the distal portion of the device includes a piston head, and wherein placing the distal portion of the device inside the subject's GI tract lumen comprises: inflating the piston head so as to form and maintain a pressure seal with a wall of the GI tract lumen, and advancing the piston head distally through the GI tract by applying, to an external surface of the piston head, fluid pressure from a fluid pressure source.

In some embodiments, the device includes a distal end of a passageway configured to convey fluid into a colon of the subject and wherein placing the distal portion of the device inside the subject's GI tract lumen comprises placing the distal portion of the passageway into the subject's colon and conveying fluid into the subject's colon.

In some embodiments, the method comprises sealing a conduit connecting between a fluid pressure source and the piston head to prevent fluid flow from the fluid pressure source to the piston head, to thereby enabling measuring an intra-abdominal pressure level. The method may comprise partially deflating the piston head inside the subject's colon to increase the accuracy of the intra-abdominal pressure level measurement.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1A is a schematic simplified illustration of the monitoring system of the present invention;

FIG. 1B is a schematic simplified illustration of the same at the calibration stage;

FIGS. 8-9 are graphs showing the pressure at the distal portion of a device, determined experimentally in accordance with an alternative embodiment of the present invention.

DETAILED DESCRIPTION OF EMBODIMENTS

Generally, it should be understood that in a laminar flow, the flow rate is determined according to Equation 1 wherein $\Delta P$ is the pressure gradient, R is the resistance and Q is the flow rate.

$$Q = \frac{\Delta P}{R} \qquad \text{Equation 1}$$

Reference is made to FIG. 1A, illustrating a flow resistor 43 enclosed in between two pressure sensors 40 and 42 measuring the pressure drop across the resistor 43.

The flow rate is equal for each of the segments enclosing the flow resistors 43 and 49 illustrated in FIG. 1A. Thus:

$$Q = \frac{P1 - P2}{R1} = \frac{P2 - P3}{R2} \Rightarrow P3 = P2 - \frac{R2}{R1}(P1 - P2)$$

where $P_1$ and $P_2$ are the pressure of the sensors pressure sensors 40 and 42 respectively; $P_3$ is the pressure in the body lumen and/or in the disposable device's balloons; $R_1$ and $R_2$ are the flow resistors' resistance of flow resistor 43 and 49 respectively.

In order to evaluate the pressure in the body lumen and/or in the disposable device's balloons, the R2/R1 ratio needs to be calculated.

Reference is made to FIG. 1B illustrating a calibration set-up used to calculate the resistance ratio and, if required, to calibrate each device prior to operation. The calibration set-up comprises the system of FIG. 1A, and a canister. During the calibration process, the canister is pressurized to a certain pressure and depressurized right after that, back to atmospheric pressure. The pressure changes $P_1$, $P_2$ and $P_3$ are measured by the sensors pressure sensors 40 and 42 and 41.

A two dimensional array of points is created when:

[x points, y points]=[$P_1$–P2 samples, $P_2$–$P_3$ samples].

A chart is then created using this array of points.

Figure 2:
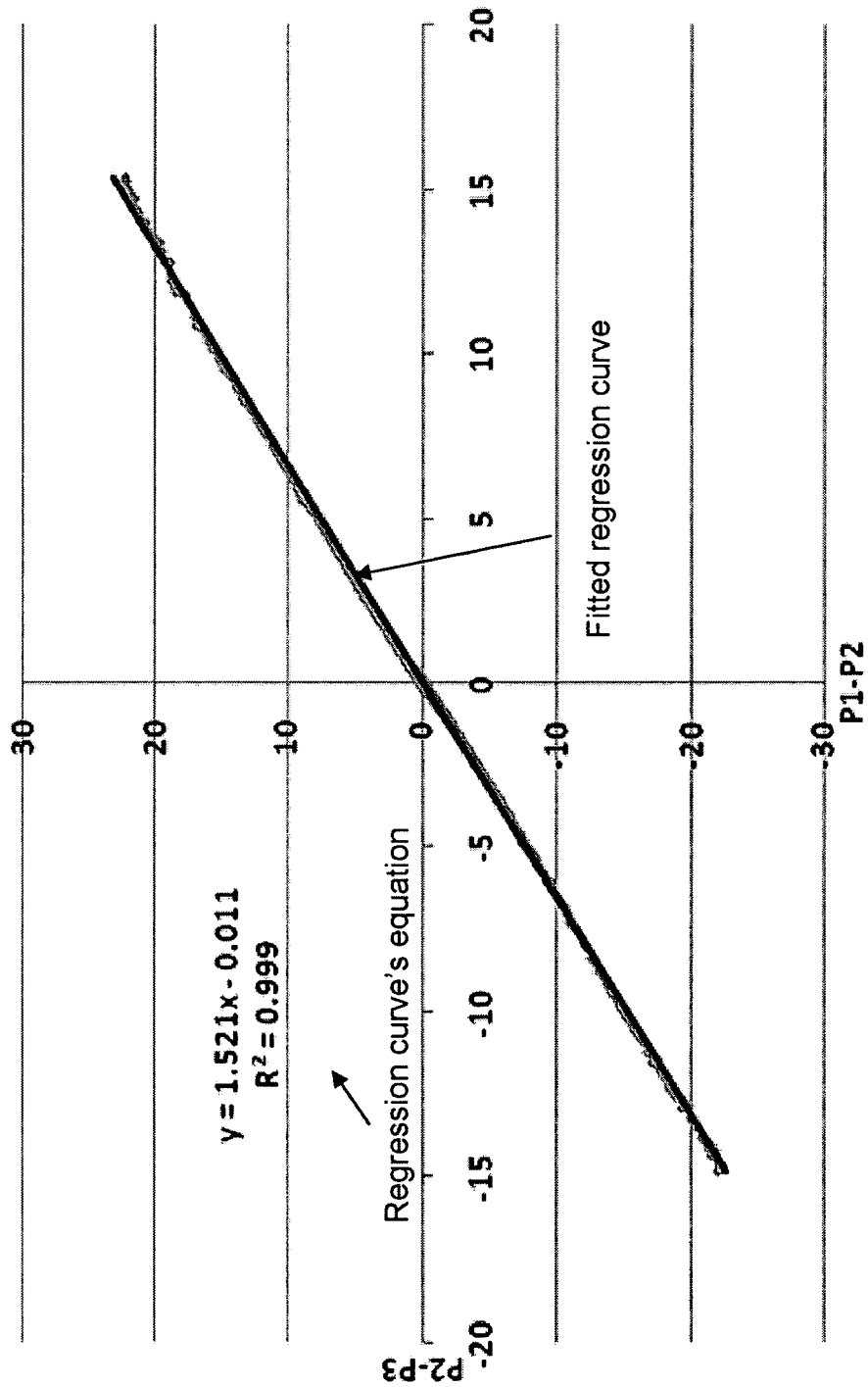
FIG. 2 is an example of a calibration chart used in the technique of the present invention.

An example of calibration chart is provided in FIG. 2.

To extricate the resistance ratio R2/R1, a regression curve (linear) is fitted with an array of points: y=ax+b, wherein a is estimated as the R2/R1 resistance ratio. The pressure at the canister can be calculated as: $P_3=P_2-a(P_1-P_2)$.

For non-laminar flows or for higher accuracy, the method is extended as follows: polynomial regression curves ($2^{nd}$ degree and higher) can be fitted for the [$P_1$–$P_2$, $P_2$–$P_3$] array of points. Thus, the pressure at the canister can be calculated as:

$$P_3 = P_2 - a_1(P_1-P_2)^i - a_2(P_1-P_2)^{i-1} - a_3(P_1-P_2)^{i-2} \ldots -a_i(P_1-P_2),$$ when $i$ is equal to the regression polynomial's degree.

Reference is now made to FIGS. 3A-3C and 4, which are schematic illustrations of a monitoring system 100 of the present invention for use with a body of a subject. The system 100 comprises a medical device 20, having a portion thereof configured to be placed inside the subject's body and two pressure sensors 40 and 42 (in the present example) accommodated remotely from the subject's body at two different spaced-apart positions outside the subject's body. In this specific and non-limiting example, the pressure sensors 40 and 42 are disposed in a proximal portion 26 of a medical device 20. In some embodiments, the medical device 20 is disposable. The medical device 20 may also configured as a two-part device, the two parts being attachable to one another, thereby enabling the part of the device containing said portion which is to be placed inside the subject's body, to be disposable.

The two pressure sensors 40 and 42 are configured and operable to detect pressure at the two spaced-apart remote positions. In particular, first sensor 40 is accommodated at a first position of proximal portion 26 of medical device 20 and detects pressure $P_1$ at the first position. Second sensor 42 is accommodated at a second position of the proximal portion of the medical device and detects pressure $P_2$ at the second position.

The two pressure sensors 40 and 42 are in fluid communication with at least one site inside the subject's body. By determining a relation between the pressure at said at least one site and the pressures $P_1$ and $P_2$ at said two spaced-apart remote positions, output data indicative of the fluid pressure at said at least one site is obtained.

Figure 3A:
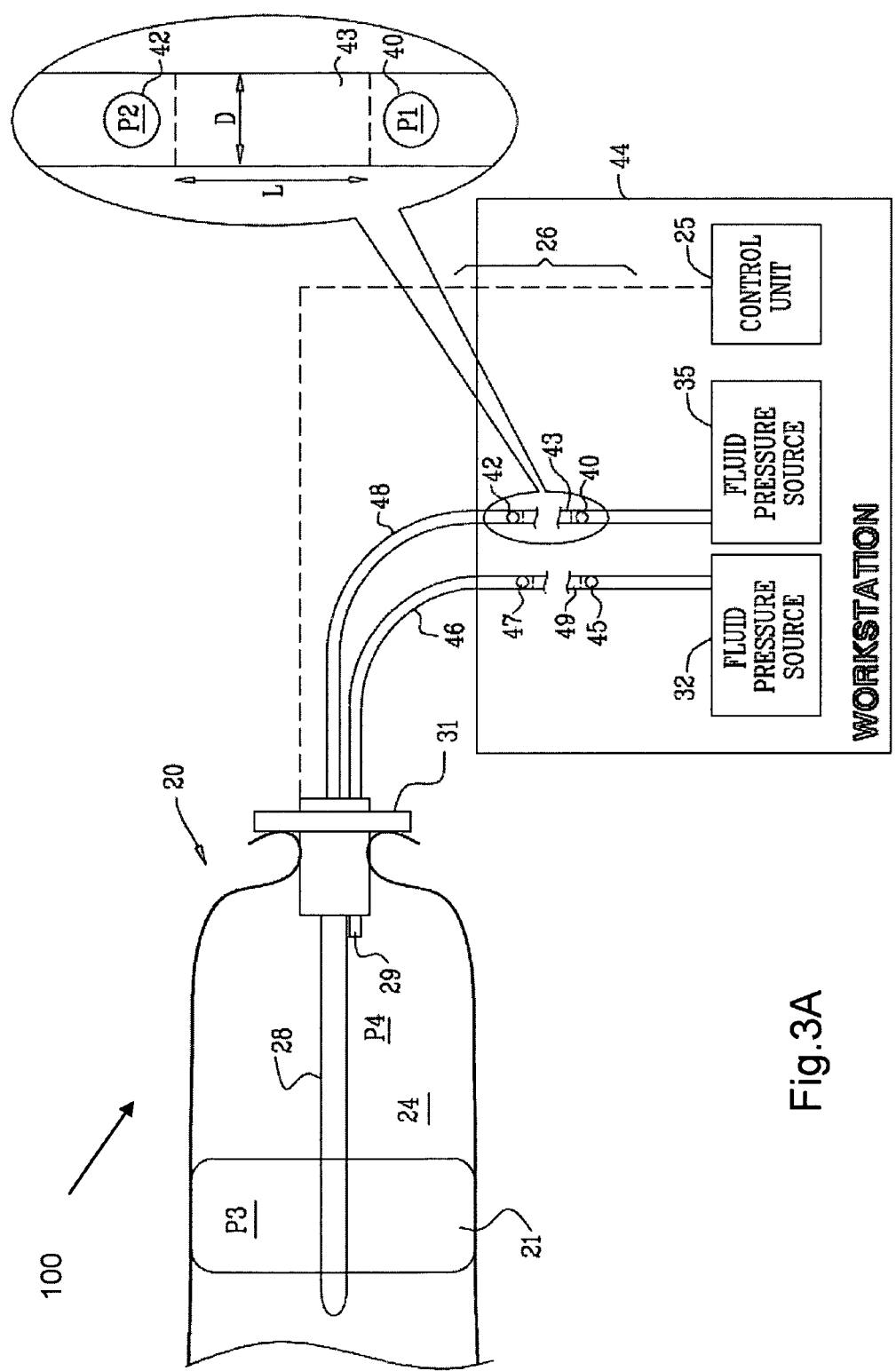
FIG. 3A is a schematic illustration of pressure sensors disposed in a proximal portion of a device, in accordance with an embodiment of the present invention.
Figure 3B:
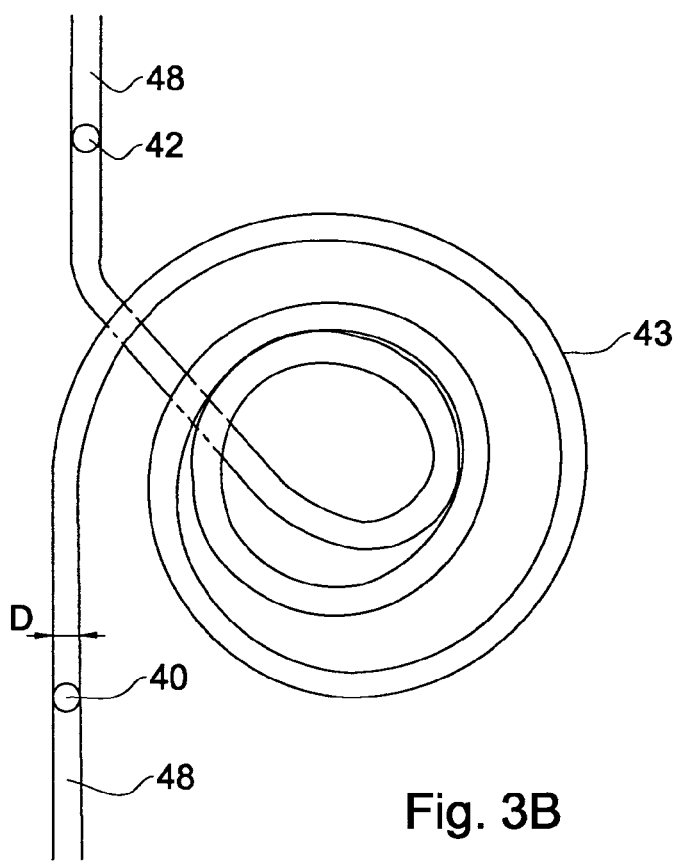
FIGS. 3B-3C are schematic illustrations of tubes that act as fluid-resistors, in accordance with respective embodiments of the present invention.
Figure 3C:
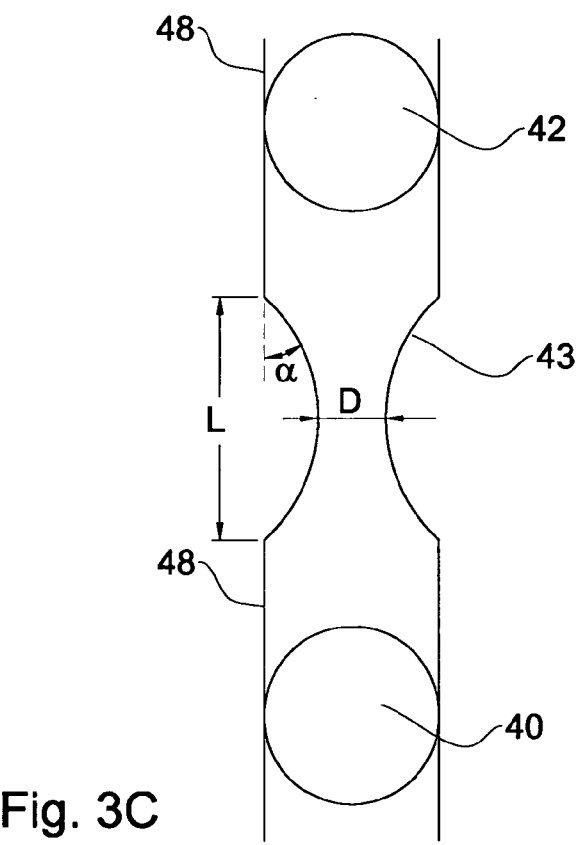

In some embodiments, the first position is at the proximal end of a tubular-like member 43, and the second position is at the distal end of the tubular-like member 43. A portion of the device extending from the second position to the distal portion of the device actually defines a distal flow path. For some applications, the tubular-like member connecting between the two pressure sensors is shaped either as shown in FIG. 3B (i.e., as a coil), or as shown in FIG. 3C (i.e., as a venturi tube). The tubular-like member is configured and operable as a flow resistor. The two pressure sensors 40 and 42 measure a pressure drop across the resistor. The model utilizes then a relation between a pressure drop across a resistor defined by a path inside the fluid communication connecting between the two pressure sensors.

In accordance with respective embodiments of the invention, tubular-like member (e.g. tube) 43 is a laminar flow resistor, causing laminar flow across the tube, or tube 43 is a turbulent flow resistor, causing fluid flow through the tube to be turbulent.

In a specific and non-limiting example, the tube 43 has a length of 278 mm and a diameter of 1.1 mm. The tube 49 has a length of 616 mm and a diameter of 2.5 mm.

In some embodiments, the monitoring system comprises a control unit 25 for monitoring and regulating fluid pressure at least one site. The control unit 25 is configured and operable to generate, an output data indicative of a pressure level $P_3$ at a site inside the subject's body (e.g. distal portion 21 of the medical device) and generates an output data indicative of the determined pressure by utilizing a model defining a relation between the pressure $P_3$ to detected pressures $P_1$ and $P_2$ at the two spaced-apart remote positions. In accordance with some embodiments of the invention, fluid flow through the device is laminar or turbulent. In some embodiments, control unit 25 is configured and operable to generate, an output data indicative of a pressure level $P_3$, such that the value of the output data varies linearly with respect to an arithmetic difference between the pressures $P_1$ and $P_2$. The relation between the pressure at one site ($P_3$) and the pressures at said two spaced-apart remote positions ($P_1$ and $P_2$) is based on mathematical function including a polynomial equation taking into account the resistance of the tubular-like member. For example, pressure $P_3$ may be determined from detected pressures $P_1$ and $P_2$, in accordance with Equation 2.

$$P_3 = P_2 - a(P_2 - P_1) + b \quad \text{(Equation 2)}$$

where a and b are calibration factors, which are determined by performing calibration experiments on the device, before the distal portion of the device is placed inside the subject's body (e.g., at the time of manufacture).

Alternatively, the control unit generates an output data indicative of a pressure $P_3$ such that the value of the output data varies non-linearly with respect to an arithmetic difference between the pressures $P_1$ and $P_2$. For example, pressure $P_3$ may be determined from detected pressures $P_1$ and $P_2$, in accordance with Equation 3.

$$P_3 = P_2 - c(P_2 - P_1) - d(P_2 - P_1)^2 + e \quad \text{(Equation 3)}$$

where c, d and e are calibration factors, which are determined by performing calibration experiments on the device, before the distal portion of the device is placed inside the subject's body.

In some embodiments, the monitoring system comprises a workstation 44 including control unit 25, which is typically a general-purpose CPU, and one or more sources of fluid 32 and 35 (i.e., liquid or gas) positive and/or negative pressure, as described hereinbelow. In some embodiments, fluid pressure sources 32 and 35 are in fluid communication with the portion of the device inside the subject's body, and control unit 25 are integrated/disposed inside the external workstation 44. Fluid is supplied to passageway 29 from fluid pressure source 32, via a first conduit 46, and to passageway 34, from fluid pressure source 35, via a second conduit 48. Fluid pressure sources 32 and 35 are configured and operable to inflate at least one site within the subject's body at predetermined pressures. First pressure sensor 40 is accommodated (e.g., attached) to a first position within conduit 48 at proximity of fluid pressure source 35. Pressure sensor 40 detects pressure $P_1$ at the first position. Second pressure sensor 42 is accommodated (e.g., attached) to a second position within passageway conduit 48 and detects pressure $P_2$ at the second position at proximity of fluid pressure source 32. Control unit 25 determines pressure $P_3$ at one site 21 based upon detected pressures $P_1$ and $P_2$, as described hereinabove.

In some embodiments, and as described hereinabove, the sensors (40 and 42) are disposed at first and second ends of tube 43, which acts as a flow resistor. Tube 43 is a continuation of conduit 48.

In some embodiments, tube 43 comprises a coiled portion of conduit 48, as shown in FIG. 3B, that is disposed inside workstation 44. In a specific and non-limiting example, the length L (shown in FIG. 3A) of the coil may be is the range of about 4 m to 8 m, e.g., 5.5 m to 6.5 m, and the inner diameter D of the coil may be is the range of about 3 mm to 5 mm (which is the same as the inner diameter of conduit 48).

For some applications, tube 43 comprises a venturi tube, as shown in FIG. 3C. In a specific and non-limiting example the venturi tube has a length in the range of about 15 mm to 30 mm (e.g., 20 mm to 25 mm), the minimum inner diameter D of the tube being 0.5 mm to 1.5 mm (e.g., 1 mm). For some applications, an angle alpha, defined by the curvature of the venturi tube, is 5 degrees to 25 degrees, e.g., 12 degrees to 18 degrees.

The ratio of the resistance to fluid flow of a portion of the device between second sensor 42 and distal portion 21, to the resistance of tube 43 to fluid flow may be determined for each different configurations of the used device. Data indicative of the pressure at the distal portion of the device may be determined utilizing a model based upon the ratio between the resistance of a distal flow path (a portion of the device extending from the second position to the distal portion of the device) to fluid flow and the resistance of the tube to fluid flow. Generally, it should be noted that if the lower the ratio is, the error level is decreased. This can usually be achieved for the auxiliary channel (conduit 48) wherein the ratio is calculated between the resistance to fluid flow of a portion of the device between sensor 47 and the distal end of passageway 29, to the resistance of tube 49 to fluid flow. The ratio of the resistance to fluid flow of a portion of the device between second sensor 42 and distal portion 21, to the resistance of tube 43 ratio is usually higher and was found to be even 4:1, but this ratio can change if the configuration of the device or the workstation change.

For example, the ratio of the resistance to fluid flow of a portion of the device between second sensor 42 and distal portion 21, to the resistance of tube 43 to fluid flow, is between 1:5 and 5:1. For some applications, the aforementioned ratio is determined before the distal portion of the device is inserted into the subject's body. Subsequently, when the distal portion of the device is inserted into the subject's body, control unit 25 determines pressure $P_3$ utilizing a model relating pressure $P_3$ to the detected pressures $P_1$ and $P_2$, and the predetermined ratio.

Tube 43 may be selected such that the pressure drop across the tube is not so large as to inhibit the functionality of the device by restricting fluid flow to the distal portion. For example, the aforementioned ratio is not less than 1.5:1. Conversely, the tube may be selected such that the pressure drop across the tube is great enough that the aforementioned ratio is not more than a given threshold, for example, 2.5:1. It should be understood that selecting a tube such that the aforementioned ratio is significantly more than 2.5:1 would result in a larger error in the calculation of pressure $P_3$ of the distal portion of the device, as a result of even small errors in the calculation of the pressure drop across the tube. Therefore, for example, the aforementioned ratio is between 1.5:1 and 2.5:1.

In some embodiments, control unit 25 dynamically determines the pressure of distal portion 21, in accordance with the techniques described hereinabove, while pressure source 35 regulates the pressure within the site 21. Fluid pressure source 35 regulates the fluid pressure within the site 21 in response to the determined pressure $P_3$. Although not represented in the figure, site 21 may include an inflatable balloon or a piston head as described in PCT Publication WO 05/065044 to Cabiri et al. Fluid flows through conduit 48 in a distal direction, when the site (e.g. piston head) is being inflated, and in a proximal direction, when the site (e.g. piston head) is being deflated.

In some embodiments, control unit 25 determines pressure $P_3$ using the same mathematical model (e.g., using a set of calibration factors) when the fluid is flowing in the distal direction, and in the proximal direction.

In other embodiments, control unit 25 determines pressure $P_3$ using a first mathematical model (e.g., using a first set of calibration factors) when the fluid is flowing in the distal direction, and using a second mathematical model (e.g., using a second set of calibration factors) when the fluid is flowing in the proximal direction. The control unit 25 may utilize respective models for determining pressure $P_3$, when fluid is flowing through conduit 48 in respective directions, in order to account for fluid flow dynamics within the tube, which vary depending on the direction in which the fluid is flowing.

In some embodiments, the direction of fluid flow through conduit 48 changes rapidly, for example, every 100 ms, and control unit 25 rapidly changes the mathematical model that it utilizes to determine $P_3$, in response to the rapid change in the direction of fluid flow.

In some embodiments, the direction of the fluid flow may change rapidly as part of a control loop for controlling the pressure inside the site (e.g. piston head). In some embodiments, the control unit 25 detects a change in the direction of the fluid flow. For example, the control unit 25 may detect that pressure $P_1$ changes from being greater than pressure $P_2$ (indicating that fluid is flowing distally) to being less than pressure $P_2$ (indicating that fluid is flowing proximally). In response to detecting the change in the direction of the fluid flow, the control unit 25 stops utilizing a first mathematical model, and starts utilizing a second mathematical model to determine pressure $P_3$.

In some embodiments, medical device 20 is a colonoscope, and comprises a piston head. In such embodiments, the piston head, and other portions of the monitoring system described herein, are generally similar to the piston head and system described in PCT Publication WO 05/065044 to Cabiri et al.

In some embodiments, the medical device 20 includes a guide member 31 at least partially insertable into a lumen of a subject's body, for example, a GI tract lumen 24. An elongate carrier 28 is inserted into the lumen. An image-capturing device 30 (shown in FIG. 4) is mounted on carrier 28 distal to piston head 21.

Guide member 31 is formed with a first passageway 29 connected to a fluid pressure source 32, which is a source of a pressurized biologically-compatible fluid, such as but not limited to, a source of pressurized air, CO2 or water. Guide member 31 may include at least one inflatable balloon in fluid communication with the guide member 31.

In some embodiments, the site inside the subject's body comprises at least one of the followings: at least one inflatable balloon being configured and operable to propel the medical device through the body lumen, a piston head propelling the medical device through the body lumen, or a portion of a body lumen.

In some embodiments, the medical device 20 include at least one auxiliary inflatable balloon or piston head, which may be fixed axially to the carrier 28 at a fixed or variable distance from the first-mentioned piston head or inflatable balloon. The carrier 28 may then include a third passageway in fluid communication with the auxiliary piston head, which may be connected to a source of fluid pressure for inflating the auxiliary piston head. There is then provided an additional pair of pressure sensor is in fluid communication with the auxiliary inflatable balloon or piston head accommodated at two different spaced-apart positions outside the subjects body and configured and operable to detect pressure at the two spaced-apart remote positions. The monitoring system of the present invention enables to determine an additional relation between the pressure at the auxiliary inflatable balloon or piston head and the pressures at the two spaced-apart remote positions being thereby indicative of the fluid pressure at the auxiliary inflatable balloon or piston head.

Carrier 28 may include a second passageway 34 (shown in FIG. 4) in fluid communication with site 21 (e.g. piston head), connected to a fluid pressure source 35, which is a source of fluid pressure for inflating site 21 (e.g. piston head). For some applications, the fluid pressure source 35 is regulated to maintain a generally constant pressure within site 21 (e.g. piston head), regardless of changes of volume of the piston head which occur in response to diameter changes of GI tract lumen 24.

As described in the '044 PCT publication, piston head 21 is typically advanced through the GI tract by applying pressure to the piston head, by passing fluid (e.g., air) into the portion of the GI tract that is proximal to the piston head, via passageway 29. During advancement of the piston head, a vent tube 38 (shown in FIG. 4) vents to the outside (i.e., to proximal to guide member 31) the pressure that accumulates due to the advancement of the piston head. The piston head is typically withdrawn proximally through the GI tract by creating a pressure difference in a reverse manner, to actively propel piston head 21 together with carrier 28 proximally. Pressurized fluid (e.g., air) from a further fluid pressure source is introduced to the distal side of piston head 21, via a pressure-application tube passing through or around piston head 21. Optionally, vent tube 38 serves as the pressure-application tube during withdrawal. The pressurized fluid creates greater fluid pressure acting on the distal side of piston head 21 than on the proximal side of piston head 21, thereby proximally propelling the piston head and the carrier. During the advancement and/or the withdrawal of the piston head through the GI tract, imaging device 30 images the GI tract.

An experiment conducted by the inventors, in which pressure of a piston head was estimated while the direction of fluid flow to the piston head was rapidly changed, is described hereinbelow, with reference to FIGS. 8 and 9.

In some embodiments, control unit 25 is used as an intra-abdominal pressure sensor, for example to determine that the pressure applied proximal to the piston head is not so great as to injure the subject. Additionally, knowing the intra-abdominal pressure indicates the minimum pressure that is useful to apply to the outer surface of the piston head in order to advance or withdraw the piston head (when the pressure is applied to the proximal or distal outer surface of the piston head, respectively).

To use the piston head as part of an intra-abdominal pressure sensor, the proximal end of conduit 48 is sealed, so that there is no fluid flow from fluid pressure source 35 to the piston head 21. This may be confirmed by checking that pressure $P_1$ detected by sensor 40 is equal to pressure $P_2$ detected by sensor 42. If there is no fluid flow, then the pressure inside the piston head 21 is substantially equal to the subject's intra-abdominal pressure. In some embodiments, before the proximal end of conduit 48 is sealed, the piston head 21 is partially deflated inside the subject's colon. Partially deflating the piston head 21 increases the accuracy of the intra-abdominal pressure measurement.

Figure 4:
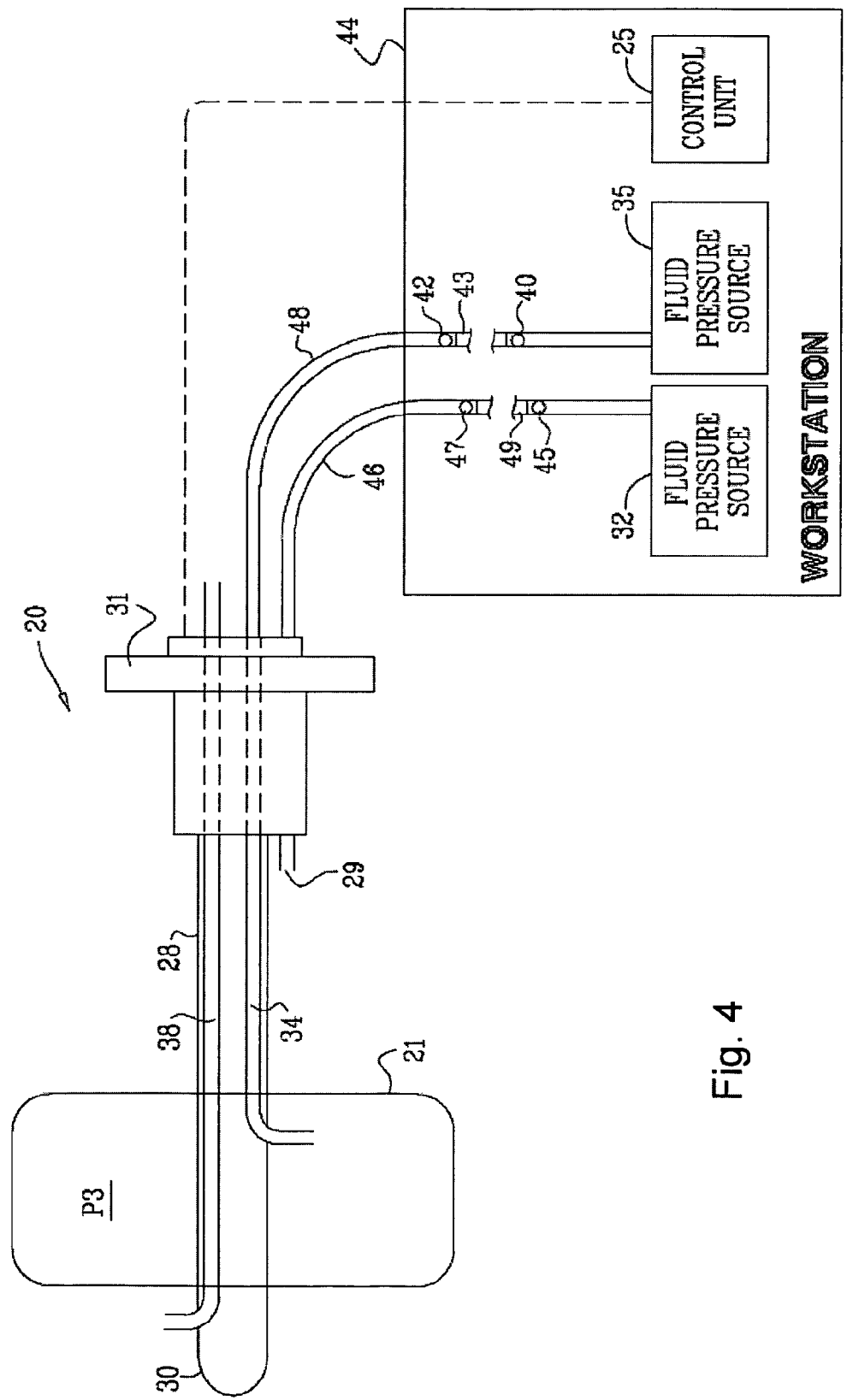
FIG. 4 is a detailed schematic illustration of pressure sensors disposed in a proximal portion of a device, in accordance with an embodiment of the present invention.

As an alternative or in addition to the above described embodiments, first and second pressure sensors (40 and 42) are placed in a different tube of the colonoscope described in the '044 publication. For example, as shown in FIGS. 3A and 4, sensors 45 and 47 may be placed at either end of a tube 49 that is a continuation of conduit 46. Sensors 45 and 47 determine a pressure $P_4$ (shown in FIG. 3A) of a portion of the subject's lumen, using the techniques described herein. In all other aspects, sensors 45 and 47 and tube 49 are generally similar to sensors 40 and 42 and tube 43 respectively.

For example, the ratio of the resistance to fluid flow of a portion of the device between sensor 47 and the distal end of passageway 29, to the resistance of tube 49 to fluid flow, is between 1:5 and 5:1. For some applications, the aforementioned ratio is determined before the distal portion end of passageway 29 is inserted into the subject's colon. Subsequently, when the distal end of passageway 29 is inserted into the subject's colon, control unit 25 determines pressure $P_4$ utilizing a model relating pressure $P_4$ to a mathematical function of the pressures detected by sensors 45 and 47, and the predetermined ratio. Tube 49 is selected such that the aforementioned ratio is about 1:1, in order for tube 49 not to limit fluid flow by too great an amount, while still creating a pressure drop across the tube. In some embodiments, tube 49 is selected such that the pressure drop across the tube is greater than the pressure drop of a portion of the device between sensor 47 and the distal end of passageway 29. For example, the aforementioned ratio may be between 1:1.7 and 1:2.3.

Although embodiments are described herein, in which device 20 is a colonoscope, and distal portion 21 of the device is a piston head, the scope of the present invention and the claims includes using the system and methods described herein with any device having a proximal portion and a distal portion, the distal portion being configured to be placed within a subject's body. For example, the scope of the present invention includes using the system and methods described herein with any colonoscopes, endoscopes, catheters, or other medical devices that are known in the art and that have a distal portion for inserting into a subject's body.

Figure 5:
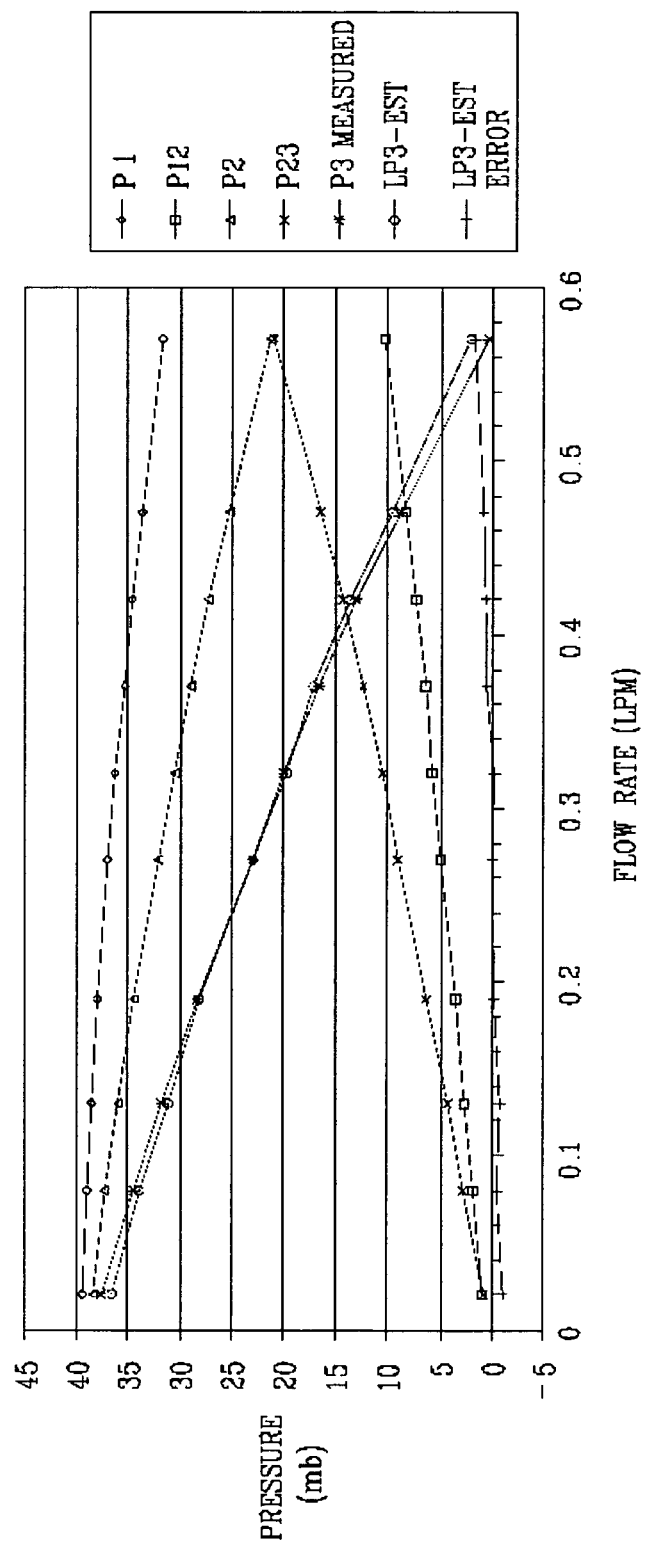
FIG. 5 is a graph showing the pressure at the distal portion of a device, determined experimentally in accordance with an embodiment of the present invention.

Reference is now made to FIG. 5, which is a graph showing pressure $P_3$ at the distal portion of a device, determined in accordance with an embodiment of the present invention. Pressures $P_1$ and $P_2$ were detected at respective positions within the proximal portion of a colonoscope. The colonoscope was as described in PCT Publication WO 05/065044, and pressures $P_1$ and $P_2$ were detected using techniques described hereinabove. The experiment was conducted while the piston head was in a simulated environment of a body lumen. The piston head was advanced through a Perspex™ tube, and a pressure sensor was placed inside the piston head to determine the actual pressure of the piston head. The length of the passageway that supplied the piston head was 2.5 m, and its diameter was 1.2 mm. A resistor tube was attached to the proximal end of the passageway, the resistor tube having a length of 2 m and a diameter of 1.8 mm. First and second pressure sensors were placed at the proximal and distal ends of the resistor tube. $P_1$ and $P_2$ were measured while fluid was supplied to the piston head at a number of different flow rates. In addition, pressure $P_3$ of the piston head of the colonoscope was measured using a pressure sensor disposed within the piston head, to give $P_3$-measured, for each of the flow rates.

In addition, pressure $P_3$ within the piston head of the colonoscope was estimated to give $LP_3$-est, using the above-mentioned linear Equation 1:

where the calibration factors a and b were determined by respectively determining the gradient and the y-intercept of a graph of ($P_2$-$P_3$-measured) against ($P_1$-$P_2$).

FIG. 5 shows plots of the following data sets versus the flow rate (in liters per minute) of fluid into the piston head:
$P_1$: detected pressure $P_1$;
$P_2$: detected pressure $P_2$;
$P_{12}$: ($P_1$-$P_2$);
$P_3$-measured: $P_3$ as measured by a pressure detector inside the piston head;
$P_{23}$: ($P_2$-$P_3$-measured);
$LP_3$-est: $P_3$ as estimated using Equation 1;
$LP_3$-est error: the difference between $P_3$ as measured ($P_3$-measured) and $P_3$ as estimated using Equation 1, i.e., the error associated with $LP_3$-est.

As is seen in FIG. 5, $LP_3$-est is quite close to $P_3$-measured, and the error in the estimate ($LP_3$-est error) is generally close to zero.

Figure 6:
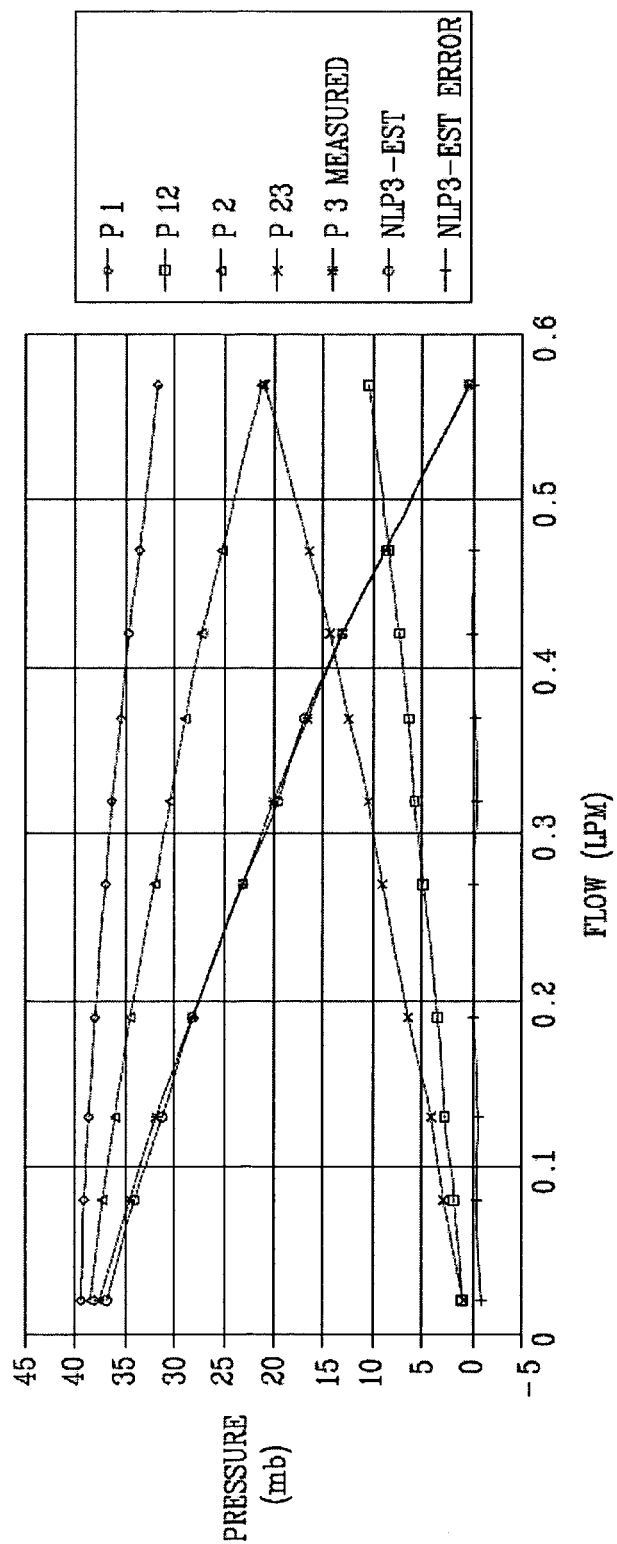
FIG. 6 is a graph showing the pressure at the distal portion of a device, determined experimentally in accordance with an alternative embodiment of the present invention.

Reference is now made to FIG. 6, which is a graph showing pressure $P_3$ at the distal portion of a device, determined in accordance with an alternative embodiment of the present invention. The measured data for the graph of FIG. 6 are the same as the measured data for that of FIG. 5. The measured data were processed to provide data set $NLP_3$-est. The pressure within the piston head of the colonoscope was estimated, using measured pressures $P_1$ and $P_2$, to give $NLP_3$-est, using the non-linear above-mentioned Equation 2:

FIG. 6 also includes a data set $NLP_3$-est error which is the difference between $P_3$ as measured by a pressure sensor disposed inside the piston head of the colonoscope ($P_3$-measured) and $P_3$ as estimated using Equation 2, i.e., the error associated with $NLP_3$-est.

As is seen in FIG. 6, $NLP_3$-est is very close to $P_3$-measured, resulting in $NLP_3$-est being very close to zero.

Figure 7:
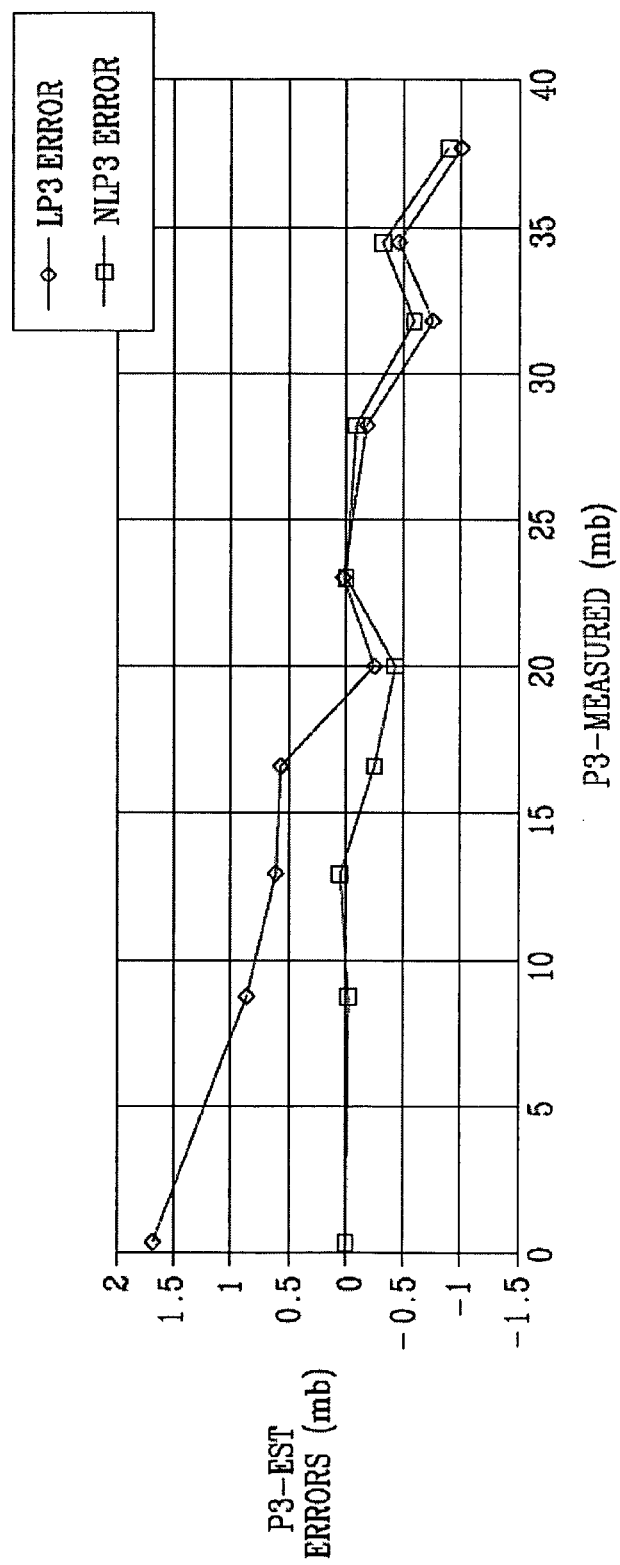
FIG. 7 is a graph showing the error associated with determining the pressure at the distal portion of a device, in accordance with respective embodiments of the present invention.

Reference is now made to FIG. 7, which is a graph showing the errors that were associated with estimating pressure $P_3$ in the experiments described with reference to FIGS. 5 and 6, in accordance with respective embodiments of the invention. FIG. 7 shows the error (in mb) associated with data sets $LP_3$-est and $NLP_3$-est plotted against the measured piston head pressure $P_3$-measured. It can be observed that, particularly for low piston head pressures, $P_3$ as estimated using non-linear equation, Equation 2, results in a smaller error in the estimation of $P_3$ than that of $P_3$ as estimated using linear equation, Equation 1. In addition, $R^2$ for the linear and the non-linear estimations of $P_3$ were evaluated. $R^2$ was 0.9942 for the linear estimation and 0.9989 for the non-linear estimation of $P_3$, indicating that the non-linear model may be a more accurate model for estimating $P_3$.

Nevertheless, even the linear model provides a reasonable estimate of the piston head pressure $P_3$. In operation of device 20, $P_3$ is estimated using a linear equation in cases when it is determined that the system behaves fully linearly, or when the accuracy provided by estimating $P_3$ using a linear equation is sufficient.

In some embodiments, following the manufacture of a given medical device, pressures $P_1$, $P_2$ are measured for that given device, using pressure sensors 40 and 42. In addition, pressure $P_3$ at the distal portion of the device is measured using a pressure sensor. Based on the measured values for $P_1$, $P_2$ and $P_3$, one or more calibration factors (for example, calibration factors a, b, c, d and/or e of Equations 1 and 2) for the given device are determined. Subsequently, when a distal portion of the device is inserted into a subject's body, control unit 25 uses the determined values of the calibration factors(s) to determine $P_3$ based upon detected pressures $P_1$ and $P_2$, in accordance with the techniques described hereinabove.

In some embodiments, during a calibration phase, the resistance of tube 43 is measured, and a ratio of the resistance of the tube to a resistance of another portion of device 20 is determined. The other portion of the device may be, for example, conduit 48 distal to sensor 42 combined with second passageway 34. Subsequently, when a distal portion of the device is inserted into a subject's body, control unit 25 uses the determined ratio to determine pressure $P_3$, based upon detected pressures $P_1$ and $P_2$, in accordance with the techniques described hereinabove.

Reference is now made to FIGS. 8-9, which are graphs showing the pressure at the distal portion of a device, as measured and as estimated, in accordance with an embodiment of the present invention. Specifically, the graph shown in FIG. 9 is an enlargement of region $R_1$ of the graph of FIG. 8. An experiment was conducted in accordance with the protocol described with reference to FIG. 5. Pressure $P_3$ in the piston head was measured and was also estimated using a non-linear model, based on detected pressures $P_1$ and $P_2$. It can be observed that, in general, the curve showing $P_3$ as estimated follows the curve showing $P_3$ as measured very closely, indicating that the methods described herein for estimating $P_3$ are accurate. In particular, with reference to FIG. 9 and region $R_1$ of FIG. 8, the results indicate that even when the pressure in the piston head changes rapidly (e.g., with a frequency of about 2 Hz, as shown) $P_3$ may be estimated very accurately using the techniques described herein.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A monitoring system for use with a body of a subject, the system comprising: a medical device, having a portion thereof configured to be placed inside the subjects body, said portion of the medical device being configured to be propelled by fluid pressure through a body lumen; at least first and second pressure sensors configured to be accommodated remotely from the subjects body at two different spaced-apart positions outside the subjects body and configured and operable to detect pressure at the two spaced-apart remote positions, respectively; said pressure sensors configured to be in fluid communication with at least one site inside the subject's body; at least one tubular member having a distal end connected to the first pressure sensor and a proximal end connected to the second pressure sensor; said tubular member being configured and operable as a flow resistor and selected to have a first characteristic resistance to fluid flow; first and second pressure sensors measuring a pressure gradient across the tubular member; a distal flow path extending between the tubular member and the medical device and exhibiting a second characteristic resistance to fluid flow; and a control unit for monitoring and regulating fluid pressure at said at least one site, said control unit utilizing a model based upon a ratio between the first characteristic resistance and the second characteristic resistance to generate an output indicative of the pressure at the at least one site.

2. The system of claim 1, wherein said medical device comprises at least one inflatable balloon; and said control unit being configured and operable to monitor and regulate fluid pressure within said at least one inflatable balloon.

3. The system of claim 2, wherein said model utilizes a relation between a pressure drop across a resistor defined by a path inside said fluid communication connecting between said at least two pressure sensors.

4. The system of claim 1, wherein said relation is based on mathematical function including a polynomial equation taking into account the resistance of said at least one tubular member.

5. The system of claim 1, wherein said medical device being configured as a two-part device, the two parts being attachable to one another, thereby enabling the part of the device containing said portion which is to be placed inside the subject's body, to be disposable.

6. The system of claim 2, wherein said control unit is integrated in an external workstation, said workstation comprising one or more fluid pressure sources in fluid communication with the portion of the device, said one or more source of fluid pressure source is configured and operable to inflate said at least one site at predetermined pressures.

7. The system of claim 1, wherein said medical device includes a guide member at least partially insertable into a body lumen, the guide member including a first passageway connectable to the source of fluid pressure, and at least one inflatable balloon in fluid communication with the guide member.

8. The system of claim 7, wherein said medical device includes a second inflatable balloon spaced apart from said at least one inflatable balloon in fluid communication with the guide member; said system comprising an additional pair of pressure sensors accommodated at two different spaced-apart auxiliary positions outside the subject's body and configured and operable to detect pressure at the two spaced-apart remote auxiliary positions; an additional relation between the pressure at the second inflatable balloon and the pressures at the two spaced-apart remote auxiliary positions being thereby indicative of the fluid pressure at the second inflatable balloon.

9. The system of claim 8, wherein at least one of said inflatable balloon and said second inflatable balloon comprises at least one piston head configured to be inflated so as to form and maintain a pressure seal with a wall of the body lumen, and be advanced distally through the body lumen in response to fluid pressure from the fluid pressure source applied to an external surface of the piston head.

10. The system of claim 2, wherein one or more fluid pressure source are configured to regulate the pressure in the device in response to the output data.

11. The system of claim 6, wherein the control unit is configured to switch between two different models based on two different directions of fluid between the fluid pressure source and the device.

12. The system of claim 6, wherein the device comprises a distal end of a passageway, the passageway being configured to convey fluid from the fluid pressure source into the body lumen.

13. A monitoring system for use with a body of a subject, the system comprising: a medical device, comprising at least one inflatable balloon and having a portion thereof configured to be placed inside the subjects body, said portion of the medical device being configured to be propelled by fluid pressure through a body lumen; at least first and second pressure sensors configured to be accommodated remotely from the subject's body at two different spaced-apart positions outside the subjects body and configured and operable to detect pressure at the two spaced-apart remote positions, respectively; said pressure sensors configured to be in fluid communication with at least one site inside the subjects body; at least one tubular member having a distal end connected to the first pressure sensor and a proximal end connected to the second pressure sensor; said tubular member being configured and operable as a flow resistor and selected to have a first characteristic resistance to fluid flow; first and second pressure sensors measuring a pressure gradient across the tubular member; a distal flow path extending between the tubular member and the medical device and exhibiting a second characteristic resistance to fluid flow; and a control unit for monitoring and regulating fluid pressure at said at least one site and within said at least one inflatable balloon; said control unit being configured and operable to generate an output indicative of a pressure level at the at least one site, utilizing at least one model based upon a ratio between the second characteristic resistance and the first characteristic resistance.

14. The system of claim 13, wherein the pressure level P3 at the at least one site is determined in accordance with the following equation:

$$P3 = P2 - \frac{R2}{R1}(P1 - P2)$$

Where P1 and P2 are the pressures measured by the pressure sensors, R2 is the second characteristic resistance and R1 is the first characteristic resistance.

15. The system of claim 13, comprising an additional pair of pressure sensor accommodated at two different spaced-apart positions outside the subject's body creating an auxiliary channel and configured and operable to detect pressure at the two spaced-apart remote positions; said control unit being configured and operable to determine an additional relation between the pressure in the auxiliary channel and the pressures at the two spaced-apart remote positions.

* * * * *

UNITED STATES PATENT AND TRADEMARK OFFICE
CERTIFICATE OF CORRECTION

PATENT NO. : 8,702,620 B2  
APPLICATION NO. : 13/126829  
DATED : April 22, 2014  
INVENTOR(S) : Ra'anan Gefen et al.

Page 1 of 1

It is certified that error appears in the above-identified patent and that said Letters Patent is hereby corrected as shown below:

Title page, item 30 insert the heading --U.S. Application Priority Data--.

Title page, beneath the aforementioned heading "U.S. Application Priority Data", insert --61/198,231, filed November 3, 2008--.

Signed and Sealed this
Twenty-fourth Day of June, 2014

Michelle K. Lee
*Deputy Director of the United States Patent and Trademark Office*